US00PP09411P

United States Patent [19]

Tachibana et al.

[11] Patent Number: Plant 9,411

[45] Date of Patent: Dec. 26, 1995

[54] VERBENA PLANT 'SUNMAREF TP-V'

[75] Inventors: Ryuichi Tachibana, Yamato; Yuji Tamura, Kofu; Ushio Sakazaki, Hikone, all of Japan

[73] Assignee: Suntory Limited, Osaka, Japan

[21] Appl. No.: 369,322

[22] Filed: Jan. 6, 1995

Related U.S. Application Data

[63] Continuation of Ser. No. 234,616, Apr. 28, 1994, abandoned, which is a continuation of Ser. No. 100,147, Aug. 2, 1993, abandoned.

[51] Int. Cl.[6] ..... A01H 5/00

[52] U.S. Cl. ..... Plt./87

[58] Field of Search ..... Plt./87

[56] References Cited

U.S. PATENT DOCUMENTS

P.P. 6,963 8/1989 Egger ..... Plt./87
P.P. 7,439 2/1991 Egger ..... Plt./87

*Primary Examiner*—James R. Feyrer
*Attorney, Agent, or Firm*—Burns, Doane, Swecker & Mathis

[57] ABSTRACT

Disclosed herein is a spreading growth habit verbena plant having long stems. The plant has abundant branching and each node in the said branches that contacts the ground commonly forms deep-spreading roots. The plant forms numerous flowers in ascending spikes with a great profusion of blooms. The flowers exhibit petals having vivid purple coloration. The plant is highly resistant to heat, cold, rain, diseases, and pests.

4 Drawing Sheets

This application is a continuation of application Ser. No. 08/234,616, filed Apr. 28, 1994 which is a continuation application of Ser. No. 08/100,147, filed Aug. 2, 1993, each now abandoned.

BACKGROUND OF THE VARIETY

The present invention relates to a new and distinct variety of verbena plant obtained from crossing 'Rainbowcarpet Brightpurple' (♀) and a wild type of verbena plant (♂) native to Brazil. The 'Rainbowcarpet Brightpurple' parent botanically is known as *Verbena×hybrida* Voss.

Verbena plants of the presently commercialized 'Rainbowcarpet' series exhibit a semi-erect growth habit having medium stems and medium branching, and a scant number of flowers in a spike, and exhibit moderate tolerances to heat and cold. Accordingly, this invention was aimed at obtaining a new variety having a spreading growth habit, much branching, numerous flowers in ascending spikes, high tolerances to heat and cold, and resistance to diseases and pests, which are superior to those of said 'Rainbowcarpet' series, and having vivid purple flower coloration.

The new variety of verbena plant according to this invention originated from a crossing of 'Rainbowcarpet Brightpurple' as the female parent and a wild type of verbena plant native to Brazil as the pollen parent, in 1988, at the Plant Biotechnology Laboratory, Institute for Fundamental Research of Suntory Ltd., residing at 2913-1 Torihara, Hakushu-cho, Kitakoma-gun, Yamanashi-ken, Japan. From this crossing 75 seedlings were obtained in 1988, from which 3 seedlings were selected, propagated by cuttings, and then grown in a trial as a bedding and planter flower during the spring of 1989. Only one of the 3 resulting plants was selected. The botanical characteristics of the finally-selected plant were then examined, using similar varieties, 'Rainbowcarpet Brightpurple,' and 'Rainbowcarpet Rose' for comparison, from the spring of 1990. As a result, it was concluded that this verbena plant is distringuishable from any other variety, whose existence is known to us, and this new variety of verbena plant was named 'Sunmaref TP-V' (Tapien Violet®).

In the following description, the color-coding is in accordance with The Horticultural Colour Chart of The Royal Horticultural Society, London, England (R.H.S. Colour Chart), and the Inter-Society Color Council-National Bureau of Standards Color Name (ISCC-NBS Color Name). A color chart based on The Japan Color Standard for Horticultural Plants (JHS Color Chart) is also added for reference.

'Rainbowcarpet Brightpurple' that was used as the female parent in the breeding of this new variety 'Sunmaref TP-V', is one of the 'Rainbowcarpet' series bred by the TAKII SEED & SEEDLING Corp., Japan. The 'Rainbowcarpet' series includes 'Rainbowcarpet Rose', 'Rainbowcarpet White', 'Rainbowcarpet Red', and the like. The main botanical characteristics of 'Rainbowcarpet Brightpurple' are as follows.

Plant:
- *Growth habit.*—Semi-erect.
- *Plant height.*—25–30 cm.
- *Spreading area of plant.*—30–35 cm.
- *Blooming period.*—Late April to November.

Stem:
- *Diameter.*—2–3 mm.
- *Anthocyanin pigmentation.*—Absent.
- *Branching.*—Medium.
- *Pubescence.*—Some pubescence is present.
- *Length of internode.*—35–40 mm.

Leaf:
- *Phyllotaxis.*—Opposite.
- *Shape of blade.*—Broadly ovate.
- *Length.*—20–25 mm.
- *Width.*—15–20 mm.
- *Depth of incision.*—Deep.
- *Color.*—Deep yellow green (R.H.S. 141A, J.H.S. 3706).
- *Pubescence.*—Some pubescence is present.

Flower:
- *Direction.*—Ascending.
- *Outward curvature of petal.*—Slightly curved.
- *Diameter.*—10–15 mm.
- *Height.*—13–15 mm.
- *Color.*—Vivid purple (R.H.S. 82A, J.H.S. 8606).
- *Color intensity.*—Absent.
- *Overlapping of petals.*—Separate.

*Spike.*—25–30 mm in length, and 30–35 mm in diameter.

*Calyx.*—0.5–1.0 cm.

*Anthocyanin pigmentation of calyx limb.*—Present.

*Peduncle.*—Less than 2 mm in diameter, and 6.0–8.0 cm in length.

*Number of flowers.*—Few (9±2).

*Productive organs.*—1 pistil and 5 stamens.

*Physiological and ecological characteristics.*—Moderate resistances to pests and diseases, and moderate tolerances to cold and heat.

The plant used as the pollen parent in the obtaining of the female parent in the breeding of this new variety 'Sunmaref TP-V' is a wild type of verbena plant native to South Brazil and this wild type of plant is presently maintained at the Plant Biotechnology Laboratory of Suntory Ltd. The main botanical characteristics of the said pollen parent are as follows.

Plant:

*Growth habit.*—Spreading.

*Plant height.*—10–15 cm.

*Plant extension.*—80–100 cm.

*Blooming period.*—Late April to November.

Stem:

*Extending.*—40–50 cm.

*Diameter.*—2–3 mm.

*Anthocyanin pigmentation.*—Absent.

*Branching.*—Abundant.

*Pubescence.*—Medium.

*Length of internode.*—20–30 mm.

Leaf:

*Phyllotaxis.*—Opposite.

*Shape of blade.*—Ovate.

*Length.*—15–20 mm.

*Width.*—10–15 mm.

*Depth of incision.*—Deep.

*Color.*—Deep yellow green (R.H.S. 141A, J.H.S. 3706).

*Pubescence.*—Medium.

Flower:

*Direction.*—Ascending.

*Outward curvature of petal.*—Slightly curved.

*Diameter.*—10–15 mm.

*Height.*—12–15 mm.

*Color.*—Brilliant purple (R.H.S. 86C, J.H.S. 8604).

*Color intensity.*—Absent.

*Overlapping of petals.*—Separate.

*Spike.*—30–40 mm in length, and 35–40 mm in diameter.

*Calyx.*—0.5–1.0 cm in length.

*Anthocyanin pigmentation of calyx limb.*—Absent.

*Peduncle.*—1–2 mm in thickness, and 30–50 mm in length.

*Number of flowers.*—Medium (10±2).

*Reproductive organs.*—1 pistil and 5 stamens.

*Physiological and ecological characteristics.*—High resistance to diseases and pests, and high tolerance to heat and cold.

This new variety of verbena plant, 'Sunmaref TP-V' was asexually reproduced by cuttings at the aforementioned Plant Biotechnology Laboratory, Institute for Fundamental Research of SUNTORY Ltd., residing at 2931-1 Torihara, Hakushu-cho, Kitakoma-gun, Yamanashi-ken, Japan, and the homogeneity and stability thereof were confirmed.

SUMMARY OF THE VARIETY

The new variety of verbena plant has a spreading growth habit with very long stems and is very low in height. The spreading area of plant is broad and thus is very different from similar varieties, 'Rainbowcarpet Brightpurple' and 'Rainbowcarpet Rose'. The plant has abundant branching, many flowers in ascending spikes, and great profusion of blooms which are clearly distinguishable from the similar varieties, 'Rainbowcarpet Brightpurple', and 'Rainbowcarpet Rose', and the whole bush remains in bloom for a considerable period of time, longer than the blooming period of 'Rainbowcarpet Rose'. The length of internode of the new variety is longer than that of similar varieties, and each node that contacts the ground commonly forms deep-spreading roots which firmly hold the plant to the ground. The flowers have petals having a vivid purple color. The plant is highly resistant to cold, heat, diseases, and pests.

DESCRIPTION OF THE VARIETY

Figure 1:
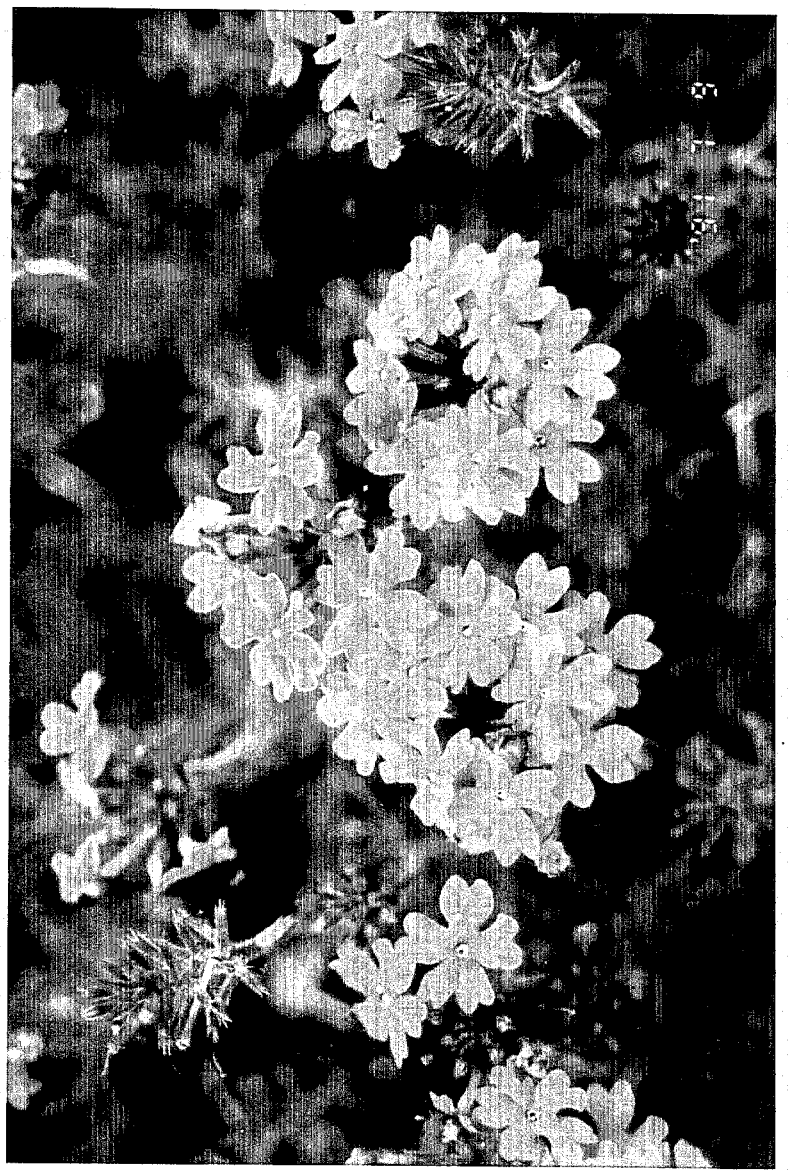
FIG. 1 is a photograph of flowers of the new variety of verbena plant.
Figure 2:
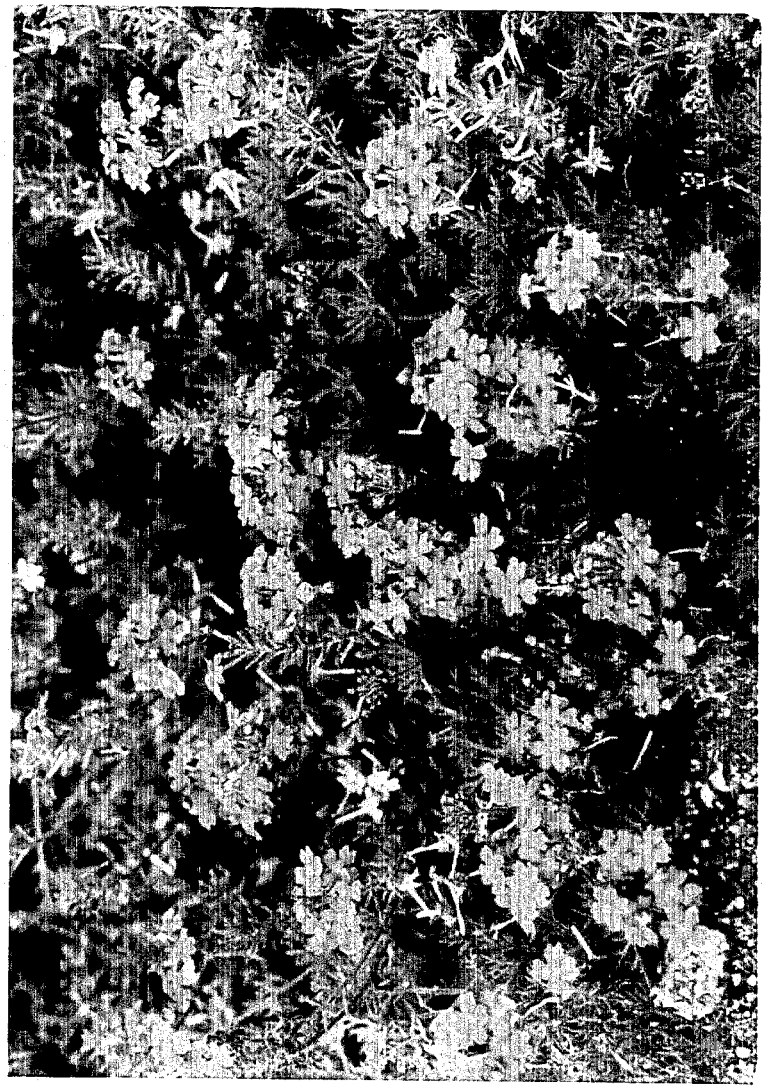
FIG. 2 is a photograph giving a partial view of the new variety of verbena plant planted in a flower bed.
Figure 3:
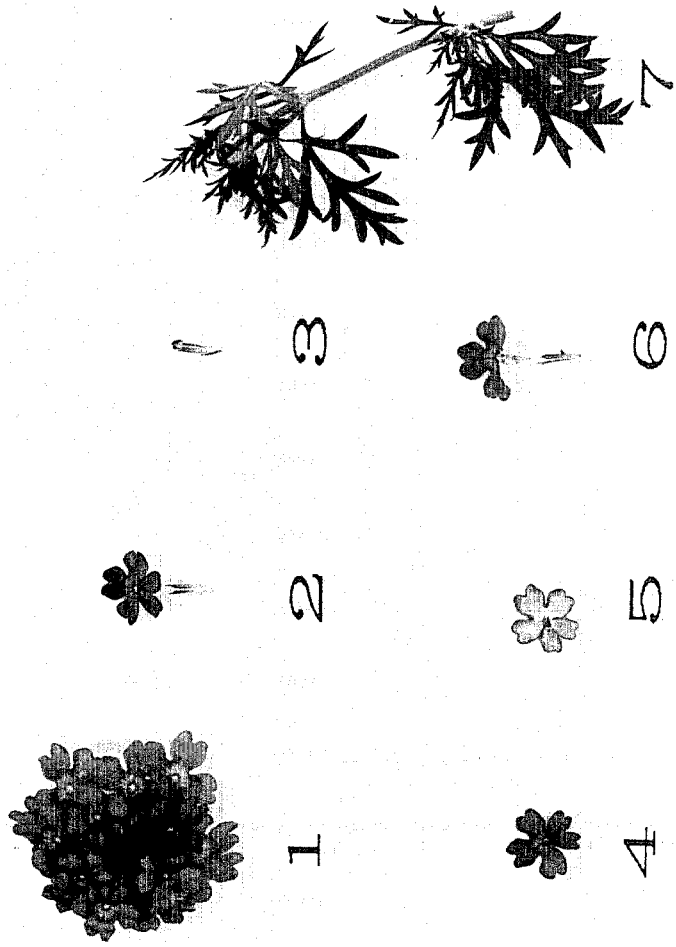
FIG. 3 is a photograph showing, in numerical order, a cluster (1), a flower (2), a bud (3), a surface view of the flower (4), a rear view of the flower (5), a cross-section view of the flower (6), and a branch (7), of the new variety of verbena plant.
Figure 4:
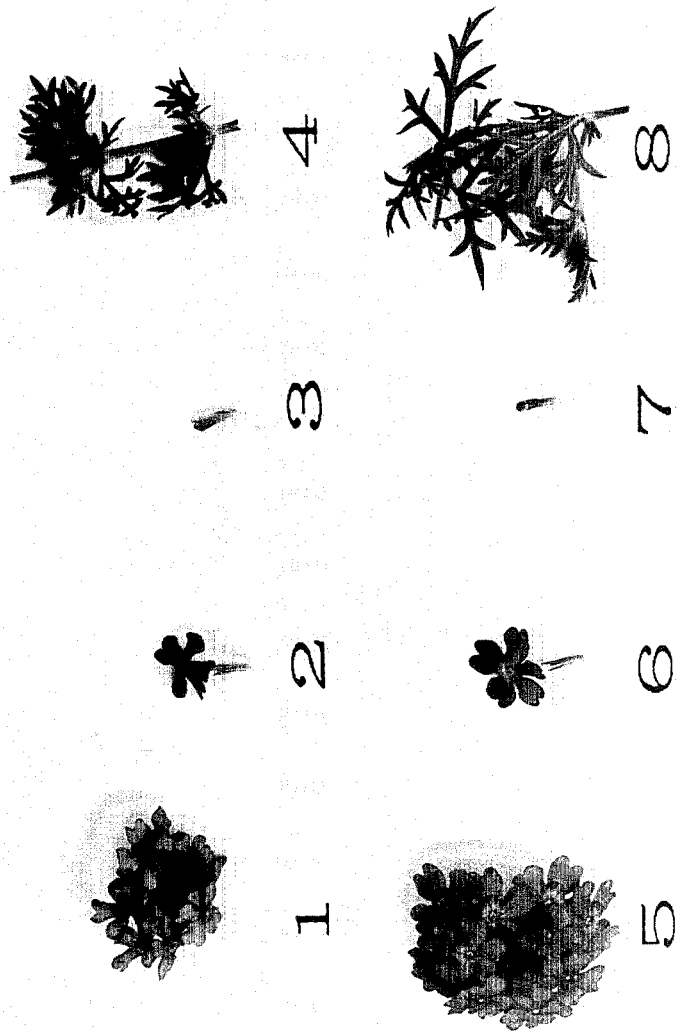
FIG. 4 is a photograph showing, a numerical order, a cluster (1), a flower (2), a bud (3), and a branch (4) of a similar variety 'Rainbowcarpet Brightpurple', in comparison with corresponding items (5–8) of the new variety of verbena plant.

The botanical characteristics of the new and distinct variety of verbena plant, 'Sunmaref TP-V' are as follows.

Plant:

*Growth habit.*—Spreading.

*Plant height.*—5–10 cm.

*Spreading area of plant.*—The stem extends to a length of 35–55 cm, and thus the spreading area of the plant is 70–110 cm.

*Growth.*—Very vigorous with abundant branching and a great profusion of blooms; the whole bush remaining in bloom for a considerable period of time.

*Blooming period.*—Late April to November, in all areas of Japan.

Stem:

*Diameter.*—1.5–2.2 mm.

*Anthocyanin pigmentation.*—Absent.

*Branching.*—Abundant; each node that contacts the ground commonly forms deep-spreading roots.

*Length of internode.*—20–50 mm.

*Pubescence.*—Medium.

Leaf:

*Phyllotaxis.*—Opposite.

*Shape of blade.*—Broadly ovate.

*Length.*—30–50 mm.

*Width.*—20–30 mm.

*Depth of incision.*—Deep.

*Color.*—Moderate yellow green (R.H.S. 147B, J.H.S. 3514).

*Pubescence.*—Medium.

Flower:

*Direction.*—Ascending.

*Outward curvature of petal.*—Slightly curved.

*Diameter.*—10–15 mm.

*Height.*—10–20 mm.

*Cluster.*—Umbel; formed from 13 flowers.

*Color.*—Vivid purple (R.H.S. 82A, J.H.S. 8607).

*Color intensity.*—Absent.

*Overlapping of petals.*—Separate.

*Spike.*—30–50 mm in length, and 40–50 mm in diameter.

*Calyx.*—0.5–1.0 cm in length. It is typical for the genus.

*Anthocyanin pigmentation of calyx limb.*—Generally present in no particular pattern.

*Peduncle.*—2–3 mm in thickness, and 5.0–10.0 cm in length.

*Number of flowers.*—Abundant. When blooming frequently each spike consists of approximately 15 open flowers and approximately 25 unopened buds. New buds form as the older flowers mature.

*Reproductive organs.*—1 pistil and 5 stamens. Seeds commonly are formed in a very low frequency.

Physiological and ecological characteristics:

High tolerance to cold and heat. The new variety is a perennial and has satisfactorily with stood temperatures as low as 0° C. and as high as 35° C. when grown in the field at Osaka, Japan. Also strong resistance to pests and diseases, particularly powdery mildew. The pinching of spent spikes commonly is necessary for a continuation of blossom production. Thinning is not required to maintain the new variety.

This new variety of verbena plant is more suitable for flower bedding and potting, particularly in planters, and is further excellent for use as a ground cover. The new variety grows well in full sun, and has no particular fertilizer requirement for good performance. The plant also grows well in the shade, but commonly does not bloom well in the absence of sunlight. A very strong resistance to mildew is exhibited by the new variety.

The plant of this new variety, 'Sunmaref TP-V' is presently planted and maintained at the Plant Biotechnology Laboratory, Institute for Fundamental Research of Suntory Ltd., residing at 2913-1 Torihara, Hakushu-cho, Kitakoma-gun, Yamanashi-ken, Japan.

We claim:

1. A new and distinct variety of verbena plant, substantially as herein illustrated and described, characterized particularly as to novelty by (A) a spreading growth habit with long stems, (B) the formation of abundant branching with each node of said spreading branches that contacts the ground commonly forming deep-spreading roots, (C) the formation of many flowers borne on ascending spikes to create a great profusion of blooms, (D) the formation of flowers that have petals which exhibit a vivid purple coloration and (E) a high resistance to heat, cold, rain diseases and pests.

* * * * *